(12) United States Patent
Lee et al.

(10) Patent No.: US 8,716,298 B2
(45) Date of Patent: May 6, 2014

(54) COMPOSITION FOR REDUCING SKIN WRINKLES INCLUDING PDE5 INHIBITOR

(71) Applicant: SK Chemicals Co., Ltd., Gyeonggi-Do (KR)

(72) Inventors: Soo-Min Lee, Seoul (KR); Sooheun Lee, Gyeonggi-Do (KR); Keun-Ho Ryu, Seoul (KR); Bong-Yong Lee, Seoul (KR); Jae-Sun Kim, Gyeonggi-Do (KR); Jung-Hoon Oh, Seoul (KR); Ye-Ji Jeon, Gyeonggi-Do (KR)

(73) Assignee: SK Chemicals Co., Ltd., Suwon (KR)

( * ) Notice: Subject to any disclaimer, the term of this patent is extended or adjusted under 35 U.S.C. 154(b) by 0 days.

(21) Appl. No.: 13/645,182

(22) Filed: Oct. 4, 2012

(65) Prior Publication Data

US 2013/0030174 A1 Jan. 31, 2013

Related U.S. Application Data

(63) Continuation of application No. PCT/KR2011/002330, filed on Apr. 4, 2011.

(30) Foreign Application Priority Data

Apr. 5, 2010 (KR) .................. 10-2010-0030769

(51) Int. Cl.
*A61K 8/49* (2006.01)
*A61Q 19/00* (2006.01)
*A61Q 19/08* (2006.01)
*A61K 31/519* (2006.01)
*C07D 487/04* (2006.01)

(52) U.S. Cl.
USPC ....................... 514/262.1; 544/256

(58) Field of Classification Search
USPC ....................... 514/262.1; 544/256
See application file for complete search history.

(56) References Cited

U.S. PATENT DOCUMENTS

2003/0216407 A1* 11/2003 Butt et al. ............... 514/252.16

FOREIGN PATENT DOCUMENTS

| KR | 10-2001-0016165 A | 3/2001 |
|---|---|---|
| KR | 10-2002-0018566 A | 3/2002 |
| WO | 01/51042 A3 | 1/2002 |
| WO | 02/15893 A3 | 3/2003 |
| WO | 2006-042701 A1 | 4/2006 |

* cited by examiner

*Primary Examiner* — Venkataraman Balasubramanian
(74) *Attorney, Agent, or Firm* — Edwards Wildman Palmer LLP

(57) ABSTRACT

Disclosed is a composition effective in reducing skin wrinkles. The composition comprises or uses a phosphodiesterase 5 (PDE5) inhibitor as an active ingredient. Further disclosed is a method for reducing skin wrinkles using the composition.

3 Claims, 5 Drawing Sheets
(4 of 5 Drawing Sheet(s) Filed in Color)

- G1 (DMSO, 0 nM)
- G2 (Vardenafil hydrochloride, 10 nM)
- G2 (Vardenafil hydrochloride, 100 nM)
- G3 (Tadalafil, 10 nM)
- G3 (Tadalafil, 100 nM)
- G4 (Sildenafil citrate, 10 nM)
- G4 (Sildenafil citrate, 100 nM)
- G5 (L-Ascorbic acid, 35.2 μg/mL)

DMSO: Dimethyl sulfoxide
**$p < 0.01$, Significant difference from the negative control by Dunnett's t-test

COMPOSITION FOR REDUCING SKIN WRINKLES INCLUDING PDE5 INHIBITOR

CROSS-REFERENCE TO RELATED APPLICATIONS

This is a continuation application of International Application No. PCT/KR2011/002330 filed Apr. 4, 2011, which claims priority to Korean Application No. 10-2010-0030769 filed Apr. 5, 2010, which applications are incorporated herein by reference.

TECHNICAL FIELD

The present invention relates to a composition effective in reducing skin wrinkles and a method for reducing skin wrinkles using the composition.

BACKGROUND ART

Skin tends to be more susceptible to wrinkles than any other tissue because of frequent contact with various external stimuli. Particularly, facial skin is directly exposed to environmental factors such as sunlight, dry air and pollutants, and it begins to wrinkle earlier than other skin tissues.

The most characteristic change arising from the aging of skin tissues takes place in the skin matrix. Aging reduces the ability of skin fibroblasts in the dermis to create fiber and matrix components. Generally, a reduction in the amount of matrix leads to a decrease in skin thickness and deterioration of skin elasticity, causing the formation of wrinkles. That is, skin aging causes serious problems, such as elasticity loss, blood circulation disturbance and poor skin barrier function.

UV light exposure generates free radicals, reactive oxygen species (ROS), radical species derived from active carbonyl compounds, etc. in and on the skin. These active species are considered major causes of damage to skin cells. Further, the active species induce DNA damage and attack cell membrane structures, leaving age spots. Moreover, the attack of the active species causes loss of the functions of collagen and fibers to make the skin moist, soft, smooth and elastic, resulting in accelerated wrinkling. The administration of antioxidants for the removal of free radicals may also be helpful in reducing skin wrinkles. However, not all antioxidants exhibit satisfactory effects against skin wrinkling. Direct observation is desirable to better evaluate the effects of antioxidants on the reduction of skin wrinkles. Many drugs and cosmetics are currently being investigated for their potential to reduce skin wrinkles caused by external environmental factors and internal mechanisms.

SUMMARY OF THE DISCLOSURE

The present invention is designed to solve the problems of the prior art, and therefore it is an object of the present invention to provide a composition effective in reducing skin wrinkles. It is another object of the present invention to provide a method effective in reducing skin wrinkles.

In order to achieve the above objects, an aspect of the present invention provides a composition for reducing skin wrinkles, comprising a phosphodiesterase 5 (PDE5) inhibitor, or a pharmaceutically acceptable salt, solvate or hydrate thereof as an active ingredient.

Another aspect of the present invention provides a new medical-use of a phosphodiesterase 5 (PDE5) inhibitor, or a pharmaceutically acceptable salt, solvate or hydrate thereof for reducing skin wrinkles.

Still another aspect of the present invention provides a use of a phosphodiesterase 5 (PDE5) inhibitor, or a pharmaceutically acceptable salt, solvate or hydrate thereof in the manufacture of a composition (for example, medicament, functional food or cosmetics) for the improvement or reduction of skin wrinkles.

BRIEF DESCRIPTION OF DRAWINGS

The patent or application file contains at least one drawing executed in color. Copies of this patent or patent application publication with color drawing(s) will be provided by the Office upon request and payment of the necessary fee.

Other objects and aspects of the present invention will become apparent from the following description of embodiments with reference to the accompanying drawing in which.

DETAILED DESCRIPTION OF THE DISCLOSURE

Figure 1:
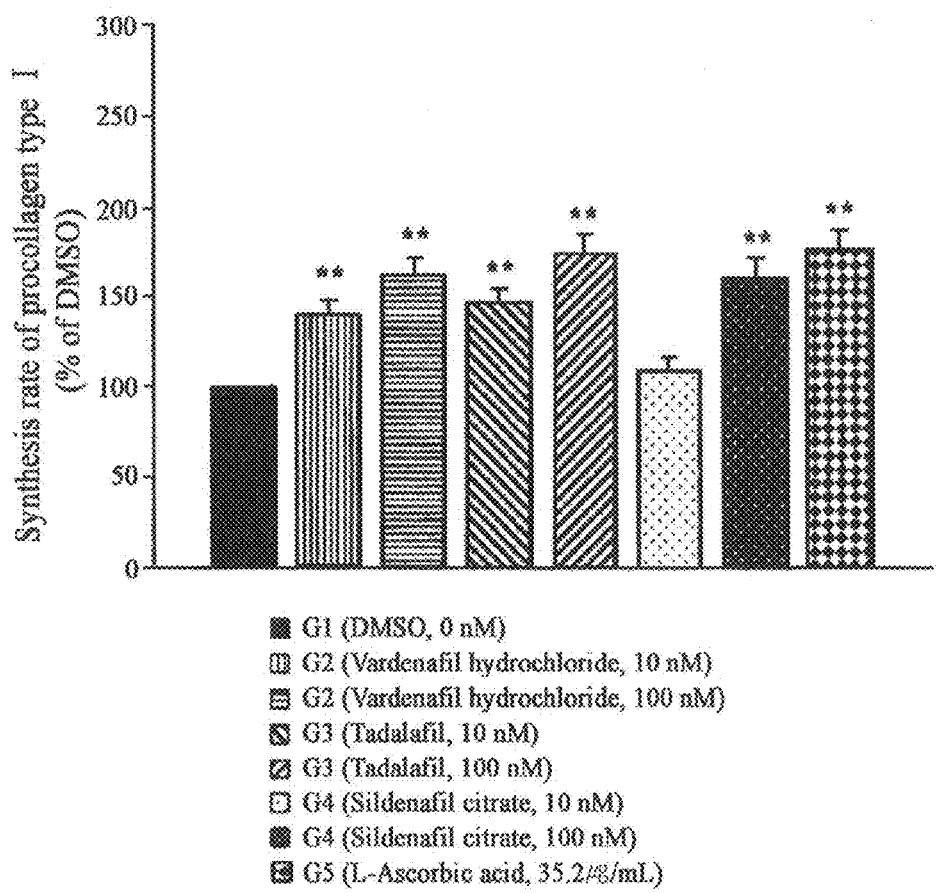
FIG. 1 graphically shows test results for the stimulatory efficacy of PDE5 inhibitors on the production of collagen having a great influence on the reduction of skin wrinkles.

Hereinafter, embodiments of the present invention will be described in detail with reference to the accompanying drawings. The embodiments of the present invention, however, may take several other forms, and the scope of the invention should not be construed as being limited to the following examples. The embodiments of the present invention are provided to more fully explain the present invention to those having ordinary knowledge in the art to which the present invention belongs.

As discussed above, in one aspect, the present invention provides a new medical-use of a phosphodiesterase 5 (PDE5) inhibitor, or a pharmaceutically acceptable salt, solvate or hydrate thereof for reducing skin wrinkles. In another aspect, the present invention provides a use of a phosphodiesterase 5 (PDE5) inhibitor, or a pharmaceutically acceptable salt, solvate or hydrate thereof in the manufacture of a composition (for example, medicament, functional food or cosmetics) for the improvement or reduction of skin wrinkles.

Phosphodiesterase refers collectively to a group of enzymes that cleave phosphodiester bonds in vivo. The PDE superfamily of enzymes is classified into 11 families, namely PDE1-PDE11, based on their amino acid sequences, substrate specificities, regulatory properties on vital reactions, pharmacological properties and tissue distribution. Of these, phosphodiesterase 5 inhibitors have been found to have a desirable influence on impotence, female sexual dysfunctions, angina pectoris, hypertension, heart failure and atherosclerosis. Particularly, phosphodiesterase 5 inhibitors are widely used in the treatment of impotence. However, the usefulness of PDE5 inhibitors, particularly those having specific structures, for the reduction of wrinkles has never been reported before. Thus, the present invention provides a novel use of PDE5 inhibitors as medicines or cosmetics for the reduction of skin wrinkles.

Examples of PDE5 inhibitors suitable for use in the composition of the present invention include 5-[2-allyloxy-5-(4-methylpiperazinylsulphonyl)phenyl]-1-methyl-3-n-propyl-1,6-dihydro-7H-pyrazolo[4,3-d]pyrimidin-7-one, 5-[2-ethoxy-5-(piperazinylsulphonyl)phenyl]-1-methyl-3-n-propyl-1,6-dihydro-7H-pyrazolo[4,3-d]pyrimidin-7-one, 5-[2-ethoxy-5-(4-methylpiperazinylsulphonyl)phenyl]-1-methyl-3-n-propyl-1,6-dihydro-7H-pyrazolo[4,3-d]pyrimidin-7-one, 5-{2-ethoxy-5-[4-(2-propyl)piperazinylsulphonyl]phenyl}-1-methyl-3-n-propyl-1,6-dihydro-7H-pyrazolo[4,3-d]pyrimidin-7-one, 5-{2-ethoxy-5-[4-(2-hydroxyethyl)piperazinylsulphonyl]phenyl}-1-methyl-3-n-propyl-1,6-dihydro-7H-pyrazolo[4,3-d]pyrimidin-7-one, 1-methyl-5-[5-(piperazinylsulphonyl)-2-n-propoxyphenyl]-3-n-propyl-1,6-dihydro-7H-pyrazolo[4,3-d]pyrimidin-7-one, 5-{5-[4-(2-hydroxyethyl)piperazinylsulphonyl]-2-n-propoxyphenyl}-1-methyl-3-n-propyl-1,6-dihydro-7H-pyrazolo[4,3-d]pyrimidin-7-one, 2-[2-ethoxy-5-(4-methyl-piperazine-1-sulphonyl)-phenyl]-5,7-dimethyl-3H-imidazo[5,1-f]-[1,2,4]triazin-4-one, 2-[2-ethoxy-5-(4-hydroxyethylpiperazine-1-sulphonyl)-phenyl]-5,7-dimethyl-3H-imidazo[5,1-f]-[1,2,4]triazin-4-one, 2-[2-ethoxy-5-(4-hydroxypiperidine-1-sulphonyl)-phenyl]-5,7-dimethyl-3H-imidazo[5,1-f][1,2,4]triazin-4-one, 2-[2-ethoxy-5-(4-hydroxymethylpiperidine-1-sulphonyl)-phenyl]-5,7-dimethyl-3H-imidazo[5,1-f][1,2,4]triazin-4-one, 2-[2-ethoxy-5-(3-hydroxypyrrolidine-1-sulphonyl)-phenyl]-5,7-dimethyl-3H-imidazo[5,1-f][1,2,4]triazin-4-one, 4-ethoxy-N-ethyl-N-(2-hydroxyethyl)-3-(5,7-dimethyl-4-oxo-3,4-dihydroimidazo[5,1-f][1,2,4]triazin-2-yl)benzenesulfonamide, N,N-diethyl-4-ethoxy-3-(5,7-dimethyl-4-oxo-3,4-dihydroimidazo[5,1-f][1,2,4]triazin-2-yl)benzenesulfonamide, 2-[2-ethoxy-5-(4-(2-pyrimidinyl)-piperazine-1-sulphonyl)-phenyl]-5,7-dimethyl-3H-imidazo-[5,1-f][1,2,4]triazin-4-one, 2-[2-ethoxy-5-(morpholine-4-sulphonyl)-phenyl]-5,7-dimethyl-3H-imidazo-[5,1-f][1,2,4]triazin-4-one, 2-[2-ethoxy-5-(1,4-dioxa-6-azaspiro[4.4]nonane-6-sulphonyl)-phenyl]-5,7-dimethyl-3H-imidazo[5,1-f][1,2,4]triazin-4-one, N,N-bis-(2-methoxyethyl)-4-ethoxy-3-(5,7-dimethyl-4-oxo-3,4-dihydro-imidazo[5,1-f][1,2,4]triazin-2-yl)-benzenesulfonamide, N-(3-isoxazolyl)-4-ethoxy-3-(5,7-dimethyl-4-oxo-3,4-dihydro-imidazo[5,1-f][1,2,4]triazin-2-yl)-benzenesulfonamide, 2-[2-ethoxy-5-(2-t-butoxycarbonylaminomethylmorpholine-4-sulphonyl)-phenyl]-5,7-dimethyl-3H-imidazo[5,1-f][1,2,4]triazin-4-one, 2-[2-ethoxy-5-(4-phenylpiperazine-1-sulphonyl)phenyl]-5,7-dimethyl-3H-imidazo[5,1-f][1,2,4]triazin-4-one, 2-[2-ethoxy-5-(3-hydroxy-3-methoxymethylpyrrolidine-1-sulphonyl)-phenyl]-5,7-dimethyl-3H-imidazo[5,1-f][1,2,4]triazin-4-one, 2-[2-ethoxy-5-(4-phenylpiperazine-1-sulphonyl)phenyl]-5-methyl-7-propyl-3H-imidazo[5,1-f][1,2,4]triazin-4-one, 2-[2-ethoxy-5-(4-ethylpiperazine-1-sulphonyl)phenyl]-5-methyl-7-propyl-3H-imidazo[5,1-f][1,2,4]triazin-4-one, 2-[2-ethoxy-5-(4-methyl-1-amino-piperazine-1-sulphonyl)phenyl]-5-methyl-7-propyl-3H-imidazo[5,1-f][1,2,4]triazin-4-one, 2-[2-ethoxy-5-(4-hydroxyethyl-1-amino-piperazine-1-sulphonyl)phenyl]-5-methyl-7-propyl-3H-imidazo[5,1-f][1,2,4]triazin-4-one, N,N-bishydroxyethylaminoethyl-4-ethoxy-3-(5-methyl(4-oxo-7-propyl-3,4-dihydro-imidazo[5,1-f][1,2,4]triazin-2-yl)benzenesulfonamide, 2-[2-ethoxy-5-(4-dimethoxyphsphorylmethyl-piperazine-1-sulphonyl)phenyl]-5-methyl-7-propyl-3H-imidazo[5,1-f][1,2,4]triazin-4-one, 2-[2-ethoxy-5-(4-diethoxyphsphorylmethyl-piperidine-1-sulphonyl)phenyl]-5-methyl-7-propyl-3H-imidazo[5,1-f][1,2,4]triazin-4-one, 2-[2-ethoxy-5-(4-hydroxy-piperidine-1-sulphonyl)phenyl]-5-methyl-7-propyl-3H-imidazo[5,1-f][1,2,4]triazin-4-one, 2-{2-ethoxy-5-[4-(4-hydroxy-ethyl)-piperazine-1-sulphonyl]phenyl}-5-methyl-7-propyl-3H-imidazo[5,1-f][1,2,4]triazin-4-one, 2-{2-ethoxy-5-[4-(3-hydroxy-propyl)-piperazine-1-sulphonyl]-phenyl}-5-methyl-7-propyl-3H-imidazo[5,1-f][1,2,4]triazin-4-one, N-allyl-4-ethoxy-N-(2-hydroxy-ethyl)-3-(5-methyl-4-oxo-7-propyl-3,4-dihydroimidazo[5,1-f][1,2,4]triazin-2-yl)benzenesulfonamide, N-ethyl-4-ethoxy-N-(2-hydroxy-ethyl)-3-(5-methyl-4-oxo-7-propyl-3,4-dihydroimidazo[5,1-f][1,2,4]triazin-2-yl)benzenesulfonamide, N,N-diethyl-4-ethoxy-3-(5-methyl-4-oxo-7-propyl-3,4-dihydro-imidazo[5,1-f][1,2,4]triazin-2-yl)benzenesulfonamide, N-(2-methoxyethyl)-3-(5-methyl-4-oxo-7-propyl-3,4-dihydro-imidazo[5,1-f][1,2,4]triazin-2-yl)-4-ethoxy-benzenesulfonamide, N-(2-N,N-dimethylethyl)-3-(5-methyl-4-oxo-7-propyl-3,4-dihydro-imidazo[5,1-f][1,2,4]triazin-2-yl)-4-ethoxy-benzenesulfonamide, N-[3-(1-morpholino)propyl]-3-(5-methyl-4-oxo-7-propyl-3,4-dihydro-imidazo[5,1-f][1,2,4]triazin-2-yl)-4-ethoxy-benzenesulfonamide, N-{3-[1-(4-methyl)piperazino]-propyl}-3-(5-methyl-4-oxo-7-propyl-3,4-dihydro-imidazo[5,1-f][1,2,4]triazin-2-yl)-4-ethoxy-benzenesulfonamide, 2-{2-ethoxy-5-[4-(2-methoxy-ethyl)-piperazine-1-sulphonyl]-phenyl}-5-methyl-7-propyl-3H-imidazo[5,1-f][1,2,4]triazin-4-one, 2-{2-ethoxy-5-[4-(2-N,N-dimethyl-ethyl)-piperazine-1-sulphonyl]-phenyl}-5-methyl-7-propyl-3H-imidazo[5,1-f][1,2,4]triazin-4-one, 2-{2-ethoxy-5-[4-(3-N,N-dimethyl-propyl)-piperazine-1-sulphonyl]-phenyl}-5-methyl-7-propyl-3H-imidazo[5,1-f][1,2,4]triazin-4-one, 2-[2-ethoxy-5-(4-dioxolano-piperidine-1-sulphonyl)-phenyl]-5-methyl-7-propyl-3H-imidazo[5,1-f][1,2,4]triazin-4-one, 2-[2-ethoxy-5-(4-(5-methyl-4-fluoroxanecarbonyl)-piperazine-1-sulphonyl)-phenyl]-5-methyl-7-propyl-3H-imidazo[5,1-f][1,2,4]triazin-4-one, 2-{2-ethoxy-5-[4-acetyl-piperazine-1-sulphonyl]-phenyl}-5-methyl-7-propyl-3H-imidazo[5,1-f][1,2,4]triazin-4-one, 2-{2-ethoxy-5-[4-formyl-piperazine-1-sulphonyl]-phenyl}-5-methyl-7-propyl-3H-imidazo[5,1-f][1,2,4]triazin-4-one, 2-[2-ethoxy-5-(3-butylsydnoneimine)-1-sulphonyl)-phenyl]-5-methyl-7-propyl-3H-imidazo[5,1-f][1,2,4]triazin-4-one, 5-methyl-2-[5-(4-methyl-piperazine-1-sulphonyl)-2-propoxy-phenyl]-7-propyl-3H-imidazo[5,1-f][1,2,4]triazin-4-one, 2-[5-(4-hydroxypiperidine-1-sulphonyl)-2-propoxy-phenyl]-5-methyl-7-propyl-3H-imidazo[5,1-f][1,2,4]triazin-4-one, 2-[5-(4-hydroxymethylpiperidine-1-sulphonyl)-2-propoxy-phenyl]-5-methyl-7-propyl-3H-imidazo[5,1-f][1,2,4]triazin-4-one, 2-{5-[4-(2-hydroxyethyl)-piperazine-1-sulphonyl]-2-propoxy-phenyl}-5-methyl-7-propyl-3H-imidazo[5,1-f][1,2,4]triazin-4-one, N-(1,1-dioxotetrahydro-1$\lambda^6$-thiophen-3-yl)-3-(5-methyl-4-oxo-7-propyl-3,4-dihydro-imidazo[5,1-f][1,2,4]triazin-2-yl)-4-propoxy-benzenesulfonamide, N-(2-dimethylaminoethyl)-N-methyl-3-(5-methyl-4-oxo-7-propyl-3,4-dihydro-imidazo[5,1-f][1,2,4]triazin-2-yl)-4-propoxy-benzenesulfonamide, 3-(5-methyl-4-oxo-7-propyl-3,4-dihydro-imidazo[5,1-f][1,2,4]triazin-2-yl)-N-(3-morpholin-4-yl-propyl)-4-propoxy-benzenesulfonamide, N,N-bis-(2-hydroxyethyl)-3-(5-methyl-4-oxo-7-propyl-3,4-dihydro-imidazo[5,1-f][1,2,4]triazin-2-yl)-4-propoxy-benzenesulfonamide, N-(3-hydroxybenzyl)-3-(5-methyl-4-oxo-7-propyl-3,4-dihydro-imidazo[5,1-f][1,2,4]triazin-2-yl)-4-propoxy-benzenesulfonamide, N-ethyl-N-(2-hydroxyethyl)-3-(5-methyl-4-oxo-7-propyl-3,4-dihydro-imidazo[5,1-f][1,2,4]triazin-2-yl)-4-propoxy-benzenesulfonamide, N-(3-ethoxypropyl)-3-(5-methyl-4-oxo-7-propyl-3,4-dihydro-imidazo[5,1-f][1,2,4]triazin-2-yl)-4-propoxy-benzenesulfonamide, 2-[5(4-hydroxypiperidine-1- sulphonyl)-2-propoxy-phenyl]-5-methyl-7-propyl-3H-imidazo[5,1-f][1,2,4]triazin-4-one, 3-(5-methyl-4-oxo-7-propyl-3,4-dihydro-imidazo[5,1-f][1,2,4]triazin-2-yl)-4-propoxy-N-pyridin-4-yl-benzenesulfonamide, N,N-diethyl-3-(5-methyl-4-oxo-7-propyl-3,4-dihydro-imidazo[5,1-f][1,2,4]triazin-2-yl)-4-propoxy-benzenesulfonamide, 1-[3-(5-methyl-4-oxo-7-propyl-3,4-dihydro-imidazo[5,1-f][1,2,4]triazin-2-yl)-4-propoxy-benzenesulphonyl]-piperidine-4-carboxylic acid, 5-methyl-2-[5-(morpholine-4-sulphonyl)-2-propoxy-phenyl]-7-propyl-3H-imidazo[5,1-f][1,2,4]triazin-4-one, N-(2-hydroxyethyl)-N-methyl-3-(5-methyl-4-oxo-7-propyl-3,4-dihydro-imidazo[5,1-f][1,2,4]triazin-2-yl)-4-propoxy-benzenesulfonamide, N-(2-hydroxyethyl)-3-(5-methyl-4-oxo-7-propyl-3,4-dihydro-imidazo[5,1-f][1,2,4]triazin-2-yl)-4-propoxy-N-propyl-benzenesulfonamide, N-[2-(3,4-dimethoxy-phenyl)ethyl]-N-methyl-3-(5-methyl-4-oxo-7-propyl-3,4-dihydro-imidazo[5,1-f][1,2,4]triazin-2-yl)-4-propoxy-benzenesulfonamide, N-allyl-N-(2-hydroxyethyl)-3-(5-methyl-4-oxo-7-propyl-3,4-dihydro-imidazo[5,1-f][1,2,4]triazin-2-yl)-4-propoxy-benzenesulfonamide, N-allyl-N-cyclopentyl-3-(5-methyl-4-oxo-7-propyl-3,4-dihydro-imidazo[5,1-f][1,2,4]triazin-2-yl)-4-propoxy-benzenesulfonamide, N-allyl-N-ethyl-3-(5-methyl-4-oxo-7-propyl-3,4-dihydro-imidazo[5,1-f][1,2,4]triazin-2-yl)-4-propoxybenzenesulfonamide, 2-[2-ethoxy-4-methoxy-5-(4-methylpiperazine-1-sulphonyl)-phenyl]-5-methyl-7-propyl-3H-imidazo[5,1-f][1,2,4]triazin-4-one, 2-{2-ethoxy-5-[4-(2-hydroxyethyl)-piperazine-1-sulphonyl]-4-methoxy-phenyl}-5-methyl-7-propyl-3H-imidazo[5,1-f][1,2,4]triazin-4-one, 4-ethoxy-N-ethyl-N-(2-hydroxyethyl)-2-methoxy-5-(5-methyl-4-oxo-7-propyl-3,4-dihydro-imidazo[5,1-f][1,2,4]triazin-2-yl)-benzenesulfonamide, 4-ethoxy-N-(4-ethoxyphenyl)-2-methoxy-5-(5-methyl-4-oxo-7-propyl-3,4-dihydro-imidazo[5,1-f][1,2,4]triazin-2-yl)-benzenesulfonamide, 4-ethoxy-N-ethyl-N-(2-hydroxyethyl)-3-(5-ethyl-4-oxo-7-propyl-3,4-dihydro-imidazo[5,1-f][1,2,4]triazin-2-yl)benzenesulfonamide, N-(2-methoxyethyl)-3-(5-ethyl-4-oxo-7-propyl-3,4-dihydro-imidazo[5,1-f][1,2,4]triazin-2-yl)-4-ethoxybenzenesulfonamide, N,N-bis-(2-methoxyethyl)-3-(5-ethyl-4-oxo-7-propyl-3,4-dihydro-imidazo[5,1-f][1,2,4]triazin-2-yl)-4-ethoxybenzenesulfonamide, 2-[5-(4-hydroxypiperidine-1-sulphonyl)-2-ethoxyphenyl]-5-ethyl-7-propyl-3H-imidazo[5,1-f][1,2,4]triazin-4-one, 2-[5-(4-hydroxymethylpiperidine-1-sulphonyl)-2-ethyl-phenyl]-5-ethyl-7-propyl-3H-imidazo[5,1-f][1,2,4]triazin-4-one, 2-{2-ethoxy-5-[4-(2-hydroxyethyl)-piperazine-1-sulphonyl]-phenyl}-5-ethyl-7-propyl-3H-imidazo[5,1-f][1,2,4]triazin-4-one, 2-[2-ethoxy-5-(4-methylpiperazine-1-sulphonyl)-phenyl]-5-ethyl-7-propyl-3H-imidazo[5,1-f][1,2,4]triazin-4-one, 3-(5-ethyl-4-oxo-7-propyl-3,4-dihydroimidazo[5,1-f][1,2,4]triazin-2-yl)-N-(3-morpholin-4-yl-propyl)-4-ethoxybenzenesulfonamide, N-(2-hydroxyethyl)-3-(5-ethyl-4-oxo-7-propyl-3,4-dihydro-imidazo[5,1-f][1,2,4]triazin-2-yl)-4-ethoxy-N-propyl-benzenesulfonamide, cis-2,3,6,7,12,12a-hexahydro-2-(4-pyridylmethyl)-6-(3,4-methylenedioxyphenyl)-pyrazino[2',1':6,1]pyrido[3,4-b]indole-1,4-dione, cis-2,3,6,7,12,12a-hexahydro-6-(2,3-dihydrobenzo[b]furan-5-yl)-2-methyl-pyrazino[2',1':6,1]pyrido[3,4-b]indole-1,4-dione, cis-2,3,6,7,12,12a-hexahydro-6-(5-bromo-2-thienyl)-2-methyl-pyrazino[2',1':6,1]pyrido[3,4-b]indole-1,4-dione, cis-2,3,6,7,12,12a-hexahydro-2-butyl-6-(4-methylphenyl)-pyrazino[2',1':6,1]pyrido[3,4-b]indole-1,4-dione, (6R,12aR)-2,3,6,7,12,12a-hexahydro-2-isopropyl-6-(3,4-methylenedioxyphenyl)-pyrazino[2',1':6,1]pyrido[3,4-b]indole-1,4-dione, (6R,12aR)-2,3,6,7,12,12a-hexahydro-2-cyclopentyl-6-(3,4-methylenedioxyphenyl)-pyrazino[2',1':6,1]pyrido[3,4-b]indole-1,4-dione, (6R,12aR)-2,3,6,7,12,12a-hexahydro-2-cyclopropylmethyl-6-(4-methoxyphenyl)-pyrazino[2',1':6,1]pyrido[3,4-b]indole-1,4-dione, (6R,12aR)-2,3,6,7,12,12a-hexahydro-6-(3-chloro-4-methoxyphenyl)-2-methyl-pyrazino[2',1':6,1]pyrido[3,4-b]indole-1,4-dione, (6R,12aR)-2,3,6,7,12,12a-hexahydro-2-methyl-6-(3,4-methylenedioxyphenyl)-pyrazino[2',1':6,1]pyrido[3,4-b]indole-1,4-dione, (6R,12aR)-2,3,6,7,12,12a-hexahydro-6-(3,4-methylenedioxyphenyl)-pyrazino[2',1':6,1]pyrido[3,4-b]indole-1,4-dione, (5aR,12R,14aS)-1,2,3,5,6,11,12,14a-octahydro-12-(3,4-methylenedioxyphenyl)-pyrrolo[1",2":4',5']pyrazino[2',1':6,1]pyrido[3,4-b]indole-5-1,4-dione, 5-[2-ethoxy-5-(isopropylamidosulphonyl)phenyl]-1-methyl-3-propyl-1,6-dihydro-7H-pyrazolo(4,3-d)pyrimidin-7-one, 5-[2-ethoxy-5-(benzylamidosulphonyl)phenyl]-1-methyl-3-isobutyl-1,6-dihydro-7H-pyrazolo(4,3-d)pyrimidin-7-one, 5-[2-propyloxy-5-(isopropylamidosulphonyl)phenyl]-1-methyl-3-propyl-1,6-dihydro-7H-pyrazolo(4,3-d)pyrimidin-7-one, 5-[2-ethoxy-5-(isopropylamidosulphonyl)phenyl]-1-ethyl-3-propyl-1,6-dihydro-7H-pyrazolo(4,3-d)pyrimidin-7-one, 5-[2-ethoxy-5-(propylamidosulphonyl)phenyl]-1-methyl-3-propyl-1,6-dihydro-7H-pyrazolo(4,3-d)pyrimidin-7-one, 5-[2-ethoxy-5-(propylamidosulphonyl)phenyl]-1-ethyl-3-propyl-1,6-dihydro-7H-pyrazolo(4,3-d)pyrimidin-7-one, 5-[2-ethoxy-5-(butylamidosulphonyl)phenyl]-1-methyl-3-propyl-1,6-dihydro-7H-pyrazolo(4,3-d)pyrimidin-7-one, 5-[2-ethoxy-5-(2-butylamidosulphonyl)phenyl]-1-methyl-3-propyl-1,6-dihydro-7H-pyrazolo(4,3-d)pyrimidin-7-one, 5-[2-ethoxy-5-(cyclopropylamidosulphonyl)phenyl]-1-methyl-3-propyl-1,6-dihydro-7H-pyrazolo(4,3-d)pyrimidin-7-one, 5-[2-ethoxy-5-(cyclopropylamidosulphonyl)phenyl]-1-ethyl-3-propyl-1,6-dihydro-7H-pyrazolo(4,3-d)pyrimidin-7-one, 5-[2-ethoxy-5-(cyclohexylamidosulphonyl)phenyl]-1-methyl-3-propyl-1,6-dihydro-7H-pyrazolo(4,3-d)pyrimidin-7-one, 5-[2-ethoxy-5-(benzylamidosulphonyl)phenyl]-1-methyl-3-propyl-1,6-dihydro-7H-pyrazolo(4,3-d)pyrimidin-7-one, 5-[2-propyloxy-5-(benzylamidosulphonyl)phenyl]-1-methyl-3-propyl-1,6-dihydro-7H-pyrazolo(4,3-d)pyrimidin-7-one, 5-[2-ethoxy-5-(benzylamidosulphonyl)phenyl]-1-ethyl-3-propyl-1,6-dihydro-7H-pyrazolo(4,3-d)pyrimidin-7-one, 5-[2-ethoxy-5-(4-fluorophenylamidosulphonyl)phenyl]-1-methyl-3-propyl-1,6-dihydro-7H-pyrazolo(4,3-d)pyrimidin-7-one, 5-[2-ethoxy-5-(4-t-butylphenylamidosulphonyl)phenyl]-1-methyl-3-propyl-1,6-dihydro-7H-pyrazolo(4,3-d)pyrimidin-7-one, 5-[2-ethoxy-5-(4-t-butylphenylamidosulphonyl)phenyl]-1-ethyl-3-propyl-1,6-dihydro-7H-pyrazolo(4,3-d)pyrimidin-7-one, 5-[2-ethoxy-5-(4-isopropylphenylamidosulphonyl)phenyl]-1-methyl-3-propyl-1,6-dihydro-7H-pyrazolo(4,3-d)pyrimidin-7-one, 5-[2-ethoxy-5-(4-fluorophenylamidosulphonyl)phenyl]-1-ethyl-3-propyl-1,6-dihydro-7H-pyrazolo(4,3-d)pyrimidin-7-one, 5-[2-ethoxy-5-(4-pyridylamidosulphonyl)phenyl]-1-methyl-3-propyl-1,6-dihydro-7H-pyrazolo(4,3-d)pyrimidin-7-one, 5-[2-propyloxy-5-(4-pyridylamidosulphonyl)phenyl]-1-methyl-3-propyl-1,6-dihydro-7H-pyrazolo(4,3-d)pyrimidin-7-one, 5-[2-ethoxy-5-(4-pyridylamidosulphonyl)phenyl]-1-ethyl-3-propyl-1,6-dihydro-7H-pyrazolo(4,3-d)pyrimidin-7-one, 5-[2-ethoxy-5-(4-pyridylamidosulphonyl)phenyl]-1-methyl-3-isobutyl-1,6-dihydro-7H-pyrazolo(4,3-d)pyrimidin-7-one, 5-[2-ethoxy-5-(3-pyridylamidosulphonyl)phenyl]-1-methyl-3-propyl-1,6-dihydro-7H-pyrazolo(4,3-d)pyrimidin-7-one, 5-[2-propyloxy-5-(3-pyridylamidosulphonyl)phenyl]-1-methyl-3-propyl-1,6-dihydro-7H-pyrazolo(4,3-d)pyrimidin-7-one, 5-[2-ethoxy-5-(3-pyridylamidosulphonyl)phenyl]-1- ethyl-3-propyl-1,6-dihydro-7H-pyrazolo(4,3-d)pyrimidin-7-one, 5-[2-ethoxy-5-(3-pyridylamidosulphonyl)phenyl]-1-methyl-3-isobutyl-1,6-dihydro-7H-pyrazolo(4,3-d)pyrimidin-7-one, 5-[2-propyloxy-5-(4-pyridylmethylamidosulphonyl)phenyl]-1-methyl-3-propyl-1,6-dihydro-7H-pyrazolo(4,3-d)pyrimidin-7-one, 5-[2-ethoxy-5-(4-pyridylmethylamidosulphonyl)phenyl]-1-methyl-3-isobutyl-1,6-dihydro-7H-pyrazolo(4,3-d)pyrimidin-7-one, 5-[2-ethoxy-5-(3-pyridylmethylamidosulphonyl)phenyl]-1-methyl-3-propyl-1,6-dihydro-7H-pyrazolo(4,3-d)pyrimidin-7-one, 5-[2-ethoxy-5-(3-pyridylmethylamidosulphonyl)phenyl]-1-methyl-3-isobutyl-1,6-dihydro-7H-pyrazolo(4,3-d)pyrimidin-7-one, 5-[2-propyloxy-5-(3-pyridylmethylamidosulphonyl)phenyl]-1-methyl-3-propyl-1,6-dihydro-7H-pyrazolo(4,3-d)pyrimidin-7-one, 5-[2-ethoxy-5-(2-pyridylmethylamidosulphonyl)phenyl]-1-methyl-3-isobutyl-1,6-dihydro-7H-pyrazolo(4,3-d)pyrimidin-7-one, 5-[2-propyloxy-5-(2-pyridylmethylamidosulphonyl)phenyl]-1-methyl-3-propyl-1,6-dihydro-7H-pyrazolo(4,3-d)pyrimidin-7-one, 5-[2-propyloxy-5-(1-methyl-3-pyrrolidinylamidosulphonyl)phenyl]-1-methyl-3-propyl-1,6-dihydro-7H-pyrazolo(4,3-d)pyrimidin-7-one, 5-[2-ethoxy-5-(1-methyl-3-pyrrolidinylamidosulphonyl)phenyl]-1-methyl-3-isobutyl-1,6-dihydro-7H-pyrazolo(4,3-d)pyrimidin-7-one, 5-[2-propyloxy-5-(1-methyl-2-pyrrolidinylmethylamidosulphonyl)phenyl]-1-methyl-3-propyl-1,6-dihydro-7H-pyrazolo(4,3-d)pyrimidin-7-one, 5-[2-ethoxy-5-(1-methyl-2-pyrrolidinylmethylamidosulphonyl)phenyl]-1-methyl-3-isobutyl-1,6-dihydro-7H-pyrazolo(4,3-d)pyrimidin-7-one, 5-[2-propyloxy-5-(1-methyl-3-pyrrolidinylmethylamidosulphonyl)phenyl]-1-methyl-3-propyl-1,6-dihydro-7H-pyrazolo(4,3-d)pyrimidin-7-one, 5-[2-ethoxy-5-(1-methyl-3-pyrrolidinylmethylamidosulphonyl)phenyl]-1-methyl-3-isobutyl-1,6-dihydro-7H-pyrazolo(4,3-d)pyrimidin-7-one, 5-[2-propyloxy-5-(1-ethyl-3-pyrrolidinylmethylamidosulphonyl)phenyl]-1-methyl-3-propyl-1,6-dihydro-7H-pyrazolo(4,3-d)pyrimidin-7-one, 5-[2-ethoxy-5-(1-ethyl-3-pyrrolidinylmethylamidosulphonyl)phenyl]-1-methyl-3-isobutyl-1,6-dihydro-7H-pyrazolo(4,3-d)pyrimidin-7-one, 5-[2-propyloxy-5-(1-methyl-2-pyrrolidinylethylamidosulphonyl)phenyl]-1-methyl-3-propyl-1,6-dihydro-7H-pyrazolo(4,3-d)pyrimidin-7-one, 5-[2-ethoxy-5-(1-methyl-2-pyrrolidinylethylamidosulphonyl)phenyl]-1-methyl-3-isobutyl-1,6-dihydro-7H-pyrazolo(4,3-d)pyrimidin-7-one, (S)-2-(2-hydroxymethyl-1-pyrrolidinyl)-4-(3-chloro-4-methoxybenzylamino)-5-[N-(2-pyrimidinylmethyl)carbamoyl]pyrimidine, 2-(6,7-dihydro-5H-pyrrolo[3,4-b]pyridin-6-yl)-4-(3-cyano-4-methoxybenzylamino)-5-[N-(2-pyrimidinylmethyl)carbamoyl]pyrimidine, 2-(5,6,7,8-tetrahydroimidazo[1,2-a]pyrazin-7-yl)-4-(3-chloro-4-methoxybenzylamino)-5-[N-(trans-4-methoxycyclohexyl)carbamoyl]pyrimidine, 2-(6,7-dihydro-5H-pyrrolo[3,4-b]pyridin-6-yl)-4-(3-cyano-4-methoxybenzylamino)-5-[N-(trans-4-hydroxycyclohexyl)carbamoyl]pyrimidine, 2-(6,7-dihydro-5H-pyrrolo[3,4-b]pyridin-6-yl)-4-(3-cyano-4-methoxybenzylamino)-5-[N-(2-morpholinoethyl)carbamoyl]pyrimidine, (S)-2-(2-hydroxymethyl-1-pyrrolidinyl)-4-(3-chloro-4-methoxybenzylamino)-5-[N-(2-morpholinoethyl)carbamoyl]pyrimidine, 2-[(2S)-2-hydroxymethyl-1-pyrrolidinyl]-4-(3-chloro-4-methoxybenzylamino)-5-[N-[[(2R)-4-methyl-2-morpholinyl]methyl]carbamoyl]-pyrimidine, 2-[(2S)-2-hydroxymethyl-1-pyrrolidinyl]-4-(3-chloro-4-methoxybenzylamino)-5-[N-[[(2S)-4-methyl-2-morpholinyl]methyl]carbamoyl]-pyrimidine, (S)-2-(2-hydroxymethyl-1-pyrrolidinyl)-4-(3-chloro-4-methoxybenzylamino)-5-[N-(4-pyrimidinylmethyl)carbamoyl]pyrimidine, 2-(4-methyl-3-oxo-1-piperazinyl)-4-(3-chloro-4-methoxybenzylamino)-5-[N-(trans-4-hydroxycyclohexyl)carbamoyl]pyrimidine, 2-(4-formyl-1-piperazinyl)-4-(3-chloro-4-methoxybenzylamino)-5-[N-(trans-4-hydroxycyclohexyl)carbamoyl]pyrimidine, 2-(5,6,7,8-tetrahydroimidazo[1,2-a]pyrazin-7-yl)-4-(3-chloro-4-methoxybenzylamino)-5-[N-(trans-4-hydroxycyclohexyl) carbamoyl]pyrimidine, 2-[cis-2,5-bis(hydroxymethyl)-1-pyrrolidinyl]-4-(3-chloro-4-methoxybenzylamino)-5-[N-(2-pyrimidinylmethyl)carbamoyl]pyrimidine, 2-(5,6,7,8-tetrahydroimidazo[1,2-a]pyrazin-7-yl)-4-(3-chloro-4-methoxybenzylamino)-5-[N-(2-pyrimidinylmethyl)carbamoyl]pyrimidine, 2-(5,6,7,8-tetrahydroimidazo[1,2-a]pyrazin-7-yl)-4-(3-chloro-4-methoxybenzylamino)-5-[N-(2-morpholinoethyl)carbamoyl]pyrimidine, 2-(5,6,7,8-tetrahydro-1,7-naphthyridin-7-yl)-4-(3-chloro-4-methoxybenzylamino)-5-[N-(2-morpholinoethyl) carbamoyl]pyrimidine, (S)-2-(2-hydroxymethyl-1-pyrrolidinyl)-4-(3-chloro-4-methoxybenzylamino)-5-acetylpyrimidine, (S)-2-(2-hydroxymethyl-1-pyrrolidinyl)-4-(3-chloro-4-methoxybenzylamino)-5-[N-(4-pyridazinylmethyl)carbamoyl]pyrimidine, (S)-2-(2-hydroxymethyl-1-pyrrolidinyl)-4-(3-chloro-4-methoxybenzylamino)-5-[N-(5-pyrimidinylmethyl)carbamoyl]pyrimidine, (S)-2-(2-hydroxymethyl-1-pyrrolidinyl)-4-(3-chloro-4-methoxybenzylamino)-5-[N-(2-pyridylmethyl)carbamoyl]pyrimidine, (S)-2-[N-(2-pyrimidinylmethyl)carbamoyl]-3-(3-chloro-4-methoxybenzylamino)-5-[2-hydroxymethyl-1-pyrrolidinyl]pyrazine, (S)-2-(2-hydroxymethyl-1-pyrrolidinyl)-4-(3-chloro-4-methoxybenzylamino)-5-[(2-morpholinoethyl)carbonyl]pyrimidine, 2-(5,6,7,8-tetrahydroimidazo[1,2-a]pyrazin-7-yl)-4-(3-chloro-4-methoxybenzylamino)-5-[N-[(4-methyl-2-morpholinyl)methyl]carbamoyl]pyrimidine, (S)-2-[N-(2-morpholinoethyl)carbamoyl]-3-(3-chloro-4-methoxybenzylamino)-5-(2-hydroxymethyl-1-pyrrolidinyl)pyrazine, 2-[N-(2-pyrimidinylmethyl)carbamoyl]-3-(3-chloro-4-methoxybenzylamino)-5-(5,6,7,8-tetrahydroimidazo[1,2-a]pyrazin-7-yl)pyrazine, (S)-2-(2-hydroxymethyl-1-pyrrolidinyl)-4-(3-chloro-4-methoxybenzylamino)-5-[(2-methoxyethyl)carbonyl]pyrimidine, (S)-2-(2-hydroxymethyl-1-pyrrolidinyl)-4-(3-chloro-4-methoxybenzylamino)-5-[N-(1,3,5-trimethyl-4-pyrazolyl)carbamoyl]pyrimidine, and pharmaceutically acceptable salts, solvates and hydrates thereof.

Sildenafil, vardenafil, tadalafil, udenafil, avanafil, or a pharmaceutically acceptable salt, solvate or hydrate thereof is the most preferred PDE5 inhibitor as an active ingredient of the composition according to the present invention.

The above-mentioned PDE5 inhibitors can be prepared by the methods disclosed in, for example, U.S. Pat. Nos. 5,250,534, 6,362,178, 5,859,006, 6,583,147, and 6,656,935, which are incorporated herein by reference in their entireties.

It is assumed that the PDE5 inhibitor used in the composition of the present invention acts on PDE5 in the skin to relax muscles and inhibits shrinkage of the relaxed muscles to effectively reduce wrinkles in a manner similar to the mechanism of BOTOX, which is currently used to reduce skin wrinkles. However, the present invention is not limited to the probable mechanism.

Some of the PDE5 inhibitors (hereinafter, also referred to simply as "compounds") can be administered in the form of pharmaceutically acceptable salts. The term "pharmaceutically acceptable salts" refers to salts that are prepared using nontoxic or relatively less toxic acids or bases. When the compounds are relatively acidic, base addition salts can be obtained by bringing neutral forms of such compounds into contact with a sufficient amount of the desired base in an inert solvent. Examples of such pharmaceutically acceptable base addition salts include, but are not limited to, lithium, sodium, potassium, calcium, ammonium, magnesium and organic amine salts. When the compounds are relatively basic, acid addition salts can be obtained by bringing neutral forms of such compounds into contact with a sufficient amount of the desired acid in an inert solvent. Examples of such pharmaceutically acceptable acid addition salts include, but are not limited to, propionic acid, isobutyric acid, oxalic acid, malic acid, malonic acid, benzoic acid, succinic acid, suberic acid, fumaric acid, mandelic acid, phthalic acid, benzenesulfonic acid, p-tolylsulfonic acid, citric acid, tartaric acid, methanesulfonic acid, hydrochloric acid, hydrobromic acid, nitric acid, carbonic acid, monohydrogencarbonic acid, phosphoric acid, monohydrogenphosphoric acid, dihydrogenphosphoric acid, sulfuric acid, monohydrogensulfuric acid, hydroiodic acid, and phosphorous acid. Other examples include, but are not limited to, salts of amino acids, such as arginate, and analogs of organic acids, such as glucuronic acid and galacturonic acid.

The compounds may exist in unsolvated forms as well as solvated forms, including hydrated forms, depending on their characteristics. The compounds may exist in crystalline or amorphous forms. Such all physical forms are encompassed within the scope of the present invention.

The compounds may exist as racemates, enantiomers, diastereomers, geometric isomers, etc. due to the presence of one or more asymmetric carbon atoms as chiral centers or one or more double bonds. These structures are also encompassed within the scope of the present invention. Some of the compounds may also exist in tautomeric forms.

The composition of the present invention can be prepared into medicines, functional foods and cosmetics. Such medicines, functional foods and cosmetics may include one or more pharmaceutically acceptable excipients or additives. The composition of the present invention may be administered alone or in combination with at least one pharmaceutically acceptable carrier or excipient, in either single or multiple doses.

The medicines, functional foods and cosmetics may be solid, liquid or semi-solid preparations. Non-limiting examples of the solid preparations include powders, granules, tablets, capsules and suppositories. The solid preparations may include suitable excipients, flavors, binders, preservatives, disintegrants, lubricants, fillers, etc. Non-limiting examples of the liquid preparations include solutions, such as aqueous solutions and propylene glycol solutions, suspensions, and emulsions. The liquid preparations may include suitable colorants, flavors, stabilizers and thickeners. Non-limiting examples of the semi-solid preparations include creams, lotions, emulsions and liniments. The semi-solid preparations may include suitable colorants, flavors, stabilizers, thickeners and surfactants. In view of the purpose of reducing skin wrinkles, which is to be achieved by the composition of the present invention, it is preferred to directly apply the composition topically to the skin because topical application reduces the possibility of side effects at other sites of the body. Therefore, it is more preferred that the composition of the present invention be formulated into semi-solid preparations.

For example, a powder may be prepared by simply mixing the compound with a suitable pharmaceutically acceptable excipient such as lactose, starch or microcrystalline cellulose. A granule may be prepared by mixing the compound, a suitable pharmaceutically acceptable excipient and a suitable pharmaceutically acceptable binder such as polyvinyl pyrrolidone or hydroxypropyl cellulose, and granulating the mixture using a suitable solvent such as water, ethanol or isopropanol (wet granulation) or by a compressive force (dry granulation). A tablet may be prepared by mixing the granule with a suitable pharmaceutically acceptable lubricant such as magnesium stearate, and compacting the mixture using a suitable tableting machine.

The composition of the present invention is preferably prepared into a general skin cosmetic formulation because it is preferred to apply the composition topically to the skin, as mentioned earlier. Specifically, the composition of the present invention can be prepared into lotions, essences, cosmetic oils, creams, powders, packs, foundations, make-up bases and cosmetic sticks. The composition of the present invention can be applied to a variety of states, such as liquids, creams, pastes and solids, which can be prepared by methods commonly known in the field of cosmetics.

For example, a lotion may be prepared by dispersing a carbomer in purified water with stirring, adding butylene glycol, glycerin and PEG-1500 to the dispersion, and mixing the mixture with a solution of polyoxyethylene cured castor oil, triethanol, a preservative and the compound in a suitable solvent such as ethanol. Alternatively, a lotion may be prepared by dissolving cetearyl alcohol, glyceryl stearate/PEG-100 stearate, Polysorbate 60, sorbitan sesquioleate, cetyl octanoate and squalene at a temperature of about 70 C.°, emulsifying the solution in a dispersion of butylene glycol, magnesium aluminum silicate, xanthan gum and a preservative in purified water at 70 C.°, cooling the emulsion, adding the emulsion to a solution of the compound in a suitable solvent or component, stirring the mixture, and cooling the mixture to room temperature.

There is no restriction on the route of administration of the composition according to the present invention. For example, the composition of the present invention may be administered orally, by injection (for example, intramuscular injection, intraperitoneal injection, intravenous injection, infusion, subcutaneous injection or implantation), by inhalation, nasally, intravaginally, rectally, sublingually, transdermally, topically, etc. depending on the type of diseases and the condition of subjects to treated. The composition of the present invention may be prepared into an appropriate unit dosage form comprising at least one known non-toxic, pharmaceutically acceptable carrier, adjuvant or vehicle, depending on the desired route of administration. The composition of the present invention may also be prepared into a depot formulation from which the active ingredient can be continuously released for a certain period of time, which is also encompassed within the scope of the present invention. In view of the purpose of reducing skin wrinkles, which is to be achieved by the composition of the present invention, a preparation for topical application is most preferred in because the composition can be directly applied to the skin.

In order to achieve the purpose of the present invention, the PDE5 inhibitor may be administered at a dose of about 0.1 mg/kg to about 200 mg/kg daily. The daily dose for the PDE5 inhibitor is preferably from about 0.5 mg/kg to about 100 mg/kg. The dose of the PDE5 inhibitor may be varied depending on the conditions of patients, e.g., age, sex and body weight, and the severity of the particular condition to be treated. For convenience of administration, if needed, the daily dose of the PDE5 inhibitor can be administered in a single dose or in divided doses. When it is intended to directly administer the compound topically to the skin, the daily dose is preferably in the range of about 0.05 mg/cm² of skin area to 50 mg/cm² of skin area, but is not limited to this range.

The present invention also provides a method for reducing skin wrinkles, comprising administering or applying to a patient in need of treatment, i.e. skin wrinkle reduction, a therapeutically or cosmetically effective amount of at least one compound selected from sildenafil, vardenafil, tadalafil, udenafil, avanafil, and pharmaceutically acceptable salts, solvates and hydrates thereof.

EXAMPLES

Hereinafter, examples of the present invention will be described in detail with reference to the accompanying drawings. The embodiments of the present invention, however, may take several other forms, and the scope of the invention should not be construed as being limited to the following examples. The embodiments of the present invention are provided to more fully explain the present invention to those having ordinary knowledge in the art to which the present invention belongs.

Example 1

Determination of Expression of PDE5 in the Skin

In this example, the expression of PDE5 in some skin tissues was determined in order to examine the ability of PDE5 inhibitors to reduce facial skin wrinkles.

Kidney and prostate tissues, where PDE5 is known to be expressed, and skin tissues were excised from male Sprague-Dawley (SD) rats, aged 7 weeks. The expression of PDE5 in tissues was confirmed by the following procedure. First, each of the tissues was cut into a piece having a weight of approximately 100 mg. Thereafter, the tissue was subjected to homogenization and RNA extraction. The RNA was quantified. 1 µg of the RNA was used for cDNA construction. The expression of PDE5 in the tissue was confirmed by real-time PCR analysis of the cDNA. β-actin was used as a control. 5'-TTGACGGATCTGGAGACGCT-3' (forward primer) and 5'-CACCACGATGGTCCAAATCA-3' (reverse primer) were used as primers for PDE5. 5'-ACCTTCAACAC-CCCAGCCA-3' (forward primer) and 5'-CAGTGGTAC-GACCAGAGGCA-3' (reverse primer) were used as primers for β-actin (see BJU INTERNATIONAL 2006 (98) 1259-1263). The relative expression levels of PDE5 in the different tissues are shown in Table 1. Data shown in Table 1 are presented as mean±standard deviation.

TABLE 1

| Kidney | Prostate | Skin |
|---|---|---|
| 0.5897 ± 0.2638 | 1.2174 ± 0.3857 | 1.4641 ± 0.3498 |

As can be seen from the results in Table 1, PDE5 was highly expressed in the skin tissues, similarly to in the kidney and prostate tissues, where PDE5 is known to be expressed at an appreciable level. These results reveal that the compounds inhibit PDE5 in the skin and can have an influence to some extent on the skin.

Example 2

Evaluation of Skin Wrinkle Reduction Effects Through Stimulatory Effects on Collagen Production In this example, stimulatory effects of major PDE5 inhibitors on collagen production were investigated in order to determine whether the PDE5 inhibitors are effective in reducing skin wrinkles. Collagen is a very important substance involved in the regulation of wrinkles. Collagen disruption is known to lead to the formation of wrinkles. Collagen production plays an important role in the reduction of wrinkles.

Normal human dermal fibroblasts (NHDFs) were cultured in a complete medium. 400 µl (1×10⁵ cells) of the NHDF culture was placed in each well of a 48-well plate and were cultured in an incubator (MCO-20 AIC, Sanyo, Japan) at 37 C.° and 5% $CO_2$ for 24 hr. After completion of culturing, the culture fluid was discarded from the wells. 500 µl of D-phosphate buffered saline (D-PBS) was added to each well for washing. Thereafter, 800 µl of a test substance and 800 µl of a positive control were added to the corresponding wells. 800 µl of a serum-free medium supplemented with DMSO was added to the wells of a negative control. The culture was continued in an incubator at 37 C.° and 5% $CO_2$ for 48 hr. After culturing was completed, the culture fluids were collected from the wells, followed by centrifugation (25 C.°, 3,000 rpm, 10 min). The supernatants were used for the quantification of procollagen type I. After 1 mL of D-PBS was added to each well of the plate, from which the culture fluids had been removed, for washing, 30 µl of a cell lysis buffer (Lot No.: 41, Cell Signaling Technology, U.S.A) was added to each well. The plate was frozen during storage in a deep freezer (DFU-657CL, Operon, Korea) at −70 C.° for 2 hr, and thawed at room temperature. The freeze-thaw procedure was repeated twice to lyse the cells. Each of the cell lysates was collected and centrifuged (Micro 17TR, Hanil Science Industrial, Korea) (4 C.°, 13000 rpm, 30 min). The supernatant was used for total protein quantification.

40 µl of the obtained supernatant was added to each well of a 96-well plate. A standard solution from a BCA protein assay kit (Lot No.: KK140637, Pierce Biotechnology Inc., USA) was diluted stepwise to different concentrations (250, 125, 50, 25, 5 and 0 µg/mL). 40 µl of the dilute solution was added to each well. 160 µl of a reagent mixture from the assay kit was added to each well. Thereafter, the resulting mixtures were allowed to react in an incubator (NB-201V, n-Biotec, Korea) at 60 C.° for 30 min. After completion of the reaction, the absorbance of each well was measured at 562 nm using an ELISA reader (PowerWave XS, BioTek Instruments, Inc., USA). The amounts of total proteins in the wells containing the test substance, the positive control and the negative control were determined by substituting the absorbance value of each well into the standard curve equation.

100 µl of the obtained supernatant was added to each well of a 96-well plate from a procollagen type I C-peptide EIA kit (Lot No.: AB01520C, Takara Bio Inc., Japan). A standard solution from the kit was diluted stepwise to different concentrations (640, 320, 160, 80, 40, 20, 10 and 0 ng/mL). 100 µl of the dilute solution was added to each well. Thereafter, the resulting mixtures were allowed to react in an incubator at 37 C.° for 2 hr. The reaction solution was discarded from each well. The well was washed with 400 µl of PBS (x 3). 100 µl of solution 1 from the kit was added to each well. The reaction was carried out at 37 C.° for 1 hr. After completion of the reaction, the reaction solution was discarded from each well and 400 µl of PBS was added to the well for washing (×4). 100 µl of a tetramethylbenzidine (TMBZ) substrate solution from the kit was added to each well. The reaction was carried out at 30 C.° for 15 min. Thereafter, 100 µl of 1 N $H_2SO_4$ solution was added to each well to stop the reaction. The absorbance of each well was measured at 450 nm using an ELISA reader. The amounts of procollagen type I in the wells containing the test substance, the positive control and the negative control were determined by substituting the absorbance value of each well into the standard curve equation.

The amount of procollagen type I in each of the wells containing the negative control, the test substance and the positive control were corrected by dividing the procollagen type I amount by the total protein amount. The synthesis rate of procollagen type I was calculated by substituting the corrected procollagen type I amount into the following equation.

$$\text{Synthesis rate of procollagen type } I(\%) = (B-A)/B \times 100$$

where A is the procollagen type I amount of the test substance or positive control, and B is the procollagen type I amount of the negative control.

The test procedure was repeated three times. The obtained synthesis rates of procollagen type I were used for statistical analysis.

Statistical analysis on the synthesis rates of procollagen type I was done using SAS (version 9.1.3, SAS Institute Inc., Cary, N.C., U.S.A.). Bartlett's test was conducted to verify the homoscedasticity of the synthesis rates of procollagen type I (significance level=0.05). When the synthesis rates of procollagen type I were homoscedastic, one-way analysis of variance (ANOVA) was conducted (significance level=0.05). Dunnett's t-test for multiple comparisons was conducted to confirm the significance of each test group from the negative control. The results are shown in FIG. 1.

The graph of FIG. 1 shows that the synthesis rates of procollagen type I of vardenafil at concentrations of 10 and 100 nM ($p<0.01$: 10 nM=140.7±7.8%, 100 nM=162.7±10.0%) were statistically significantly increased, compared to the synthesis rate of procollagen type I of the negative control (100.0±0.0%). Further, the synthesis rates of procollagen type I of tadalafil at concentrations of 10 and 100 nM ($p<0.01$: 10 nM=147.2±8.1%, 100 nM=174.7±10.2%) were statistically significantly increased, compared to the synthesis rate of procollagen type I of the negative control (100.0±0.0%). There was no statistically significant difference in synthesis rate of procollagen type I between 10 nM sildenafil (108.6±8.1%) and the negative control (100.0±0.0%), but a statistical significant difference was observed in synthesis rate of procollagen type I between 100 nM sildenafil ($p<0.01$, 160.7±12.1%) and the negative control (100.0±0.0%). The synthesis rate of procollagen type I of the positive control at a concentration of 35.2 µg/mL (200 µM) ($p<0.01$:175.7±11.5%) was statistically significantly increased, compared to the synthesis rate of procollagen type I of the negative control (100.0±0.0%). From the test results, it can be confirmed that the PDE5 inhibitors effectively reduced the wrinkles.

Example 3

Evaluation of Wrinkle Reduction Effects in the Skin

An examination was made as to whether the PDE5 inhibitors can substantially reduce skin wrinkles of animal models. Hairless mice, aged 7 weeks, were irradiated with UVB (290-320 nm, 312 nm) to induce wrinkles. The compound or the control was applied to each mouse and its influence on the induced wrinkles was evaluated.

More specifically, the mice were irradiated with 60 mJ/cm$^2$ (1 minimal edemal dose (MED)) for 3 days weekly during the first and second week after wrinkling, 120 mJ/cm$^2$ (2 MED) for 3 days during the third week after wrinkling, 180 mJ/cm$^2$ (3 MED) for 3 days during the fourth week after wrinkling, 240 mJ/cm$^2$ (4 MED) for 3 days weekly during the fifth to eighth week after wrinkling, and 240 mJ/cm$^2$ (4 MED) for 5 days weekly during the ninth to fifteenth week after wrinkling. During the sixteenth and seventeenth week after wrinkling, about 0.5 ml of squalene-OOH, an oxidation product of squalene by UV irradiation, was applied once using a brush to induce deeper wrinkles. Thereafter, the compound or the control was applied to each mouse twice daily for 14 days. Photographs were taken of the skins and are shown in FIGS. 2-5.

Figure 2:
FIG. 2 shows photographs of a normal group (n=4) that was not irradiated with UV to induce wrinkles.

FIG. 2 shows photographs of the normal group (n=4) that was not irradiated with UV to induce wrinkles. Some shallow wrinkles were naturally formed in the normal group with increasing age of the mice.

Figure 3:
FIG. 3 shows photographs of a negative control (n=6) that was irradiated with UV to induce wrinkles and treated with a medium (20% EtOH, 30% DW, 50% PEG) only without administration of any active ingredient.

FIG. 3 shows photographs of the negative control (n=6) after UV irradiation to induce wrinkles and treated with a medium (20% EtOH, 30% DW, 50% PEG) only for 2 weeks without administration of any active ingredient. Many deep wrinkles were observed in the negative control.

Figure 4:
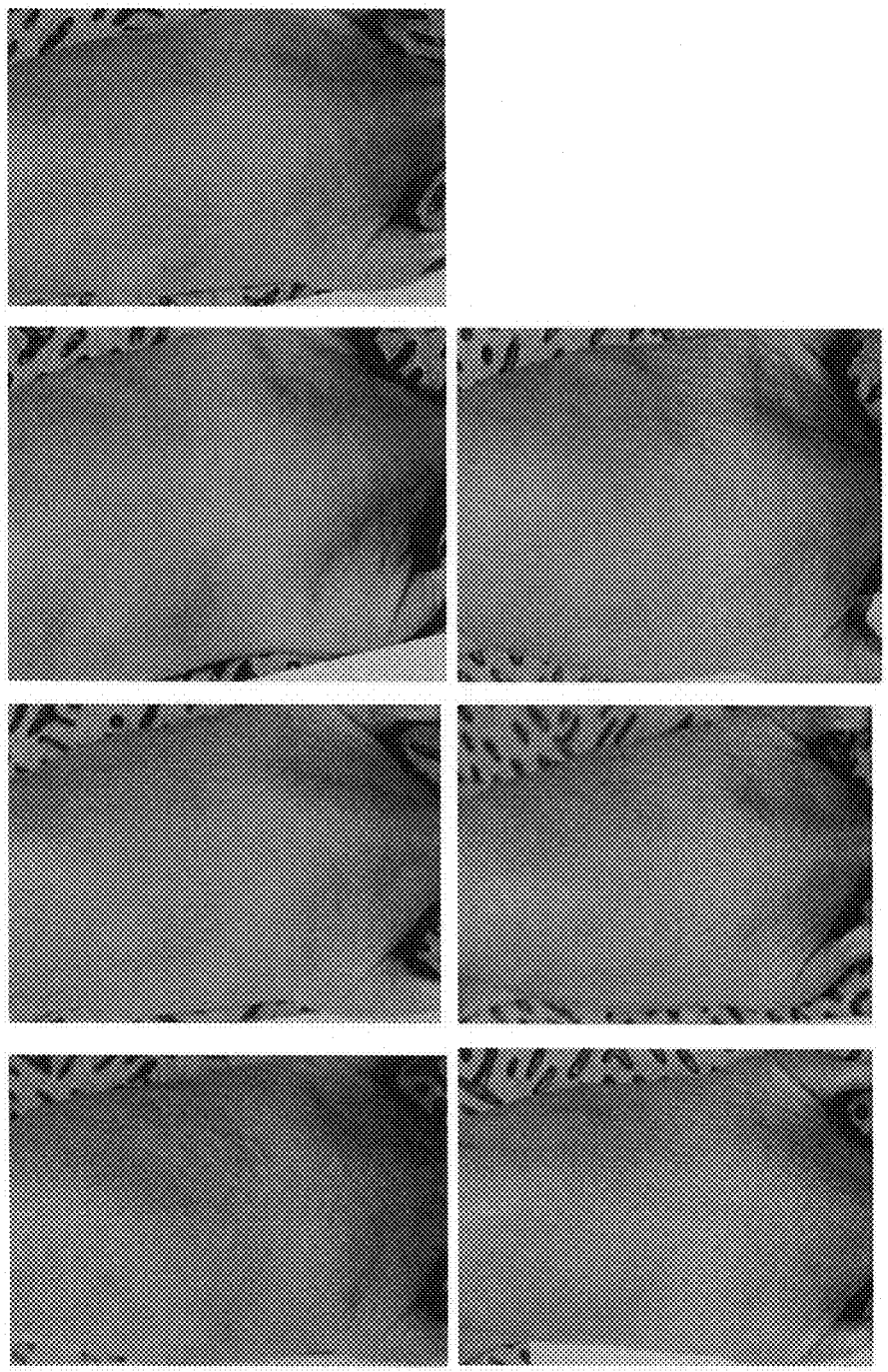
FIG. 4 shows photographs of a group (n=7) treated with 10 mM (about 5%) sildenafil after wrinkles were induced.

FIG. 4 shows photographs of the group (n=7) treated with 10 mM (about 5%) sildenafil, a representative PDE5 inhibitor, after wrinkles were induced. Wrinkle reduction was observed in the group. The skins of the group gradually became clean.

Figure 5:
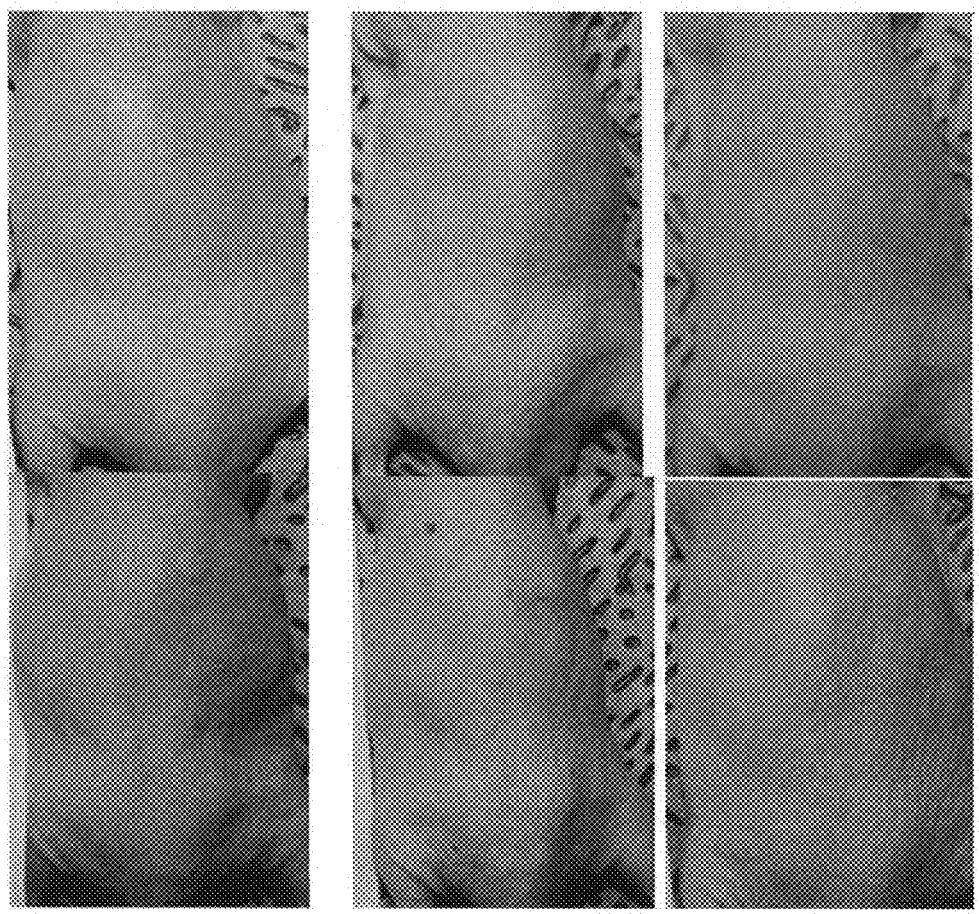
FIG. 5 shows photographs of a positive control (n=6) treated with 0.05% retinoic acid.

FIG. 5 shows photographs of the positive control (n=6) treated with 0.05% retinoic acid. Cornified layers were formed and continuously peeled. As a result of changing the frequency of applications of retinoic acid from twice to once daily, continuous formation and peeling of cornified layers were still observed. Slight wrinkle reduction was observed, but the skin was not cleaned any more and cornified layers became thicker.

The present invention has been described in detail. However, it should be understood that the detailed description and specific examples, while indicating preferred embodiments of the invention, are given by way of illustration only, since various changes and modifications within the spirit and scope of the invention will become apparent to those skilled in the art from this detailed description.

What is claimed is:

1. A method for reducing skin wrinkles through stimulatory effects on collagen production, comprising administering to a subject in need thereof a therapeutically effective amount of a phosphodiesterase 5 (PDE5) inhibitor, or a pharmaceutically acceptable salt, solvate, or hydrate thereof.

2. The method of claim 1, wherein the PDE5 inhibitor is at least one selected from the group consisting of 5-[2-allyloxy-5-(4-methylpiperazinylsulphonyl)phenyl]-1-methyl-3-n-propyl-1,6-dihydro-7H-pyrazolo[4,3-d]pyrimidin-7-one, 5-[2-ethoxy-5-(piperazinylsulphonyl)phenyl]-1-methyl-3-n-propyl-1,6-dihydro-7H-pyrazolo[4,3-d]pyrimidin-7-one, 5-[2-ethoxy-5-(4-methylpiperazinylsulphonyl)phenyl]-1-methyl-3-n-propyl-1,6-dihydro-7H-pyrazolo[4,3-d]pyrimidin-7-one, 5-{2-ethoxy-5-[4-(2-propyl)piperazinylsulphonyl]phenyl}-1-methyl-3-n-propyl-1,6-dihydro-7H-pyrazolo[4,3-d]pyrimidin-7-one, 5-{2-ethoxy-5-[4-(2-hydroxyethyl)piperazinylsulphonyl]phenyl}-1-methyl-3-n-propyl-1,6-dihydro-7H-pyrazolo[4,3-d]pyrimidin-7-one, 1-methyl-5-[5-(piperazinylsulphonyl)-2-n-propoxyphenyl]-3-n-propyl-1,6-dihydro-7H-pyrazolo[4,3-d]pyrimidin-7-one, 5-{5-[4-(2-hydroxyethyl)piperazinylsulphonyl]-2-n-propoxyphenyl}-1-methyl-3-n-propyl-1,6-dihydro-7H-pyrazolo[4,3-d]pyrimidin-7-one, 5-[2 ethoxy-5-(isopropylamidosulphonyl)phenyl]-1-methyl-3-propyl-1,6-dihydro-7H-pyrazolo(4,3-d)pyrimidin-7-one, 5-[2-ethoxy-5-(benzylamidosulphonyl)phenyl]-1-methyl-3-isobutyl-1,6-dihydro-7H-pyrazolo(4,3-d)pyrimidin-7-one, 5-[2-propyloxy-5-(isopropylamidosulphonyl)phenyl]-1-methyl-3-propyl-1,6-dihydro-7H-pyrazolo(4,3-d)pyrimidin-7-one, 5-[2-ethoxy-5-(isopropylamidosulphonyl)phenyl]-1-ethyl-3-propyl-1,6-dihydro-7H-pyrazolo(4,3-d)pyrimidin-7-one, 5-[2-ethoxy-5-(propylamidosulphonyl)phenyl]-1-methyl-3-propyl-1,6-dihydro-7H-pyrazolo(4,3-d)pyrimidin-7-one, 5-[2-ethoxy-5-(propylamidosulphonyl)phenyl]-1-ethyl-3-propyl-1,6-dihydro-7H-pyrazolo(4,3-d)pyrimidin-7-one, 5-[2-ethoxy-5-(butylamidosulphonyl)phenyl]-1-methyl-3-propyl-1,6-dihydro-7H-pyrazolo(4,3-d)pyrimidin-7-one, 5-[2-ethoxy-5-(2-butylamidosulphonyl)phenyl]-1-methyl-3-propyl-1,6-dihydro-7H-pyrazolo(4,3-d)pyrimidin-7-one, 5-[2-ethoxy-5-(cyclopropylamidosulphonyl)phenyl]-1-methyl-3-propyl-1,6-dihydro-7H-pyrazolo(4,3-d)pyrimidin-7-one, 5-[2-ethoxy-5-(cyclopropylamidosulphonyl)phenyl]-1-ethyl-3-propyl-1,6-dihydro-7H-pyrazolo(4,3-d)pyrimidin-7-one, 5-[2-ethoxy-5-(cyclohexylamidosulphonyl)phenyl]-1-methyl-3-propyl-1,6-dihydro-7H-pyrazolo(4,3-d)pyrimidin-7-one, 5-[2-ethoxy-5-(benzylamidosulphonyl)phenyl]-1-methyl-3-propyl-1,6-dihydro-7H-pyrazolo(4,3-d)pyrimidin-7-one, 5-[2-propyloxy-5-(benzylamidosulphonyl)phenyl]-1-methyl-3-propyl-1,6-dihydro-7H-pyrazolo(4,3-d)pyrimidin-7-one, 5-[2-ethoxy-5-(benzylamidosulphonyl)phenyl]-1-ethyl-3-propyl-1,6-dihydro-7H-pyrazolo(4,3-d)pyrimidin-7-one, 5-[2-ethoxy-5-(4-fluorophenylamidosulphonyl)phenyl]-1-methyl-3-propyl-1,6-dihydro-7H-pyrazolo(4,3-d)pyrimidin-7-one, 5-[2-ethoxy-5-(4-t-butylphenylamidosulphonyl)phenyl]-1-methyl-3-propyl-1,6-dihydro-7H-pyrazolo(4,3-d)pyrimidin-7-one, 5-[2-ethoxy-5-(4-t-butylphenylamidosulphonyl)phenyl]-1-ethyl-3-propyl-1,6-dihydro-7H-pyrazolo(4,3-d)pyrimidin-7-one, 5-[2-ethoxy-5-(4-isopropylphenylamidosulphonyl)phenyl]-1-methyl-3-propyl-1,6-dihydro-7H-pyrazolo(4,3-d)pyrimidin-7-one, 5-[2-ethoxy-5-(4-fluorophenylamidosulphonyl)phenyl]-1-ethyl-3-propyl-1,6-dihydro-7H-pyrazolo(4,3-d)pyrimidin-7-one, 5-[2-ethoxy-5-(4-pyridylamidosulphonyl)phenyl]-1-methyl-3-propyl-1,6-dihydro-7H-pyrazolo(4,3-d)pyrimidin-7-one, 5-[2-propyloxy-5-(4-pyridylamidosulphonyl)phenyl]-1-methyl-3-propyl-1,6-dihydro-7H-pyrazolo(4,3-d)pyrimidin-7-one, 5-[2-ethoxy-5-(4-pyridylamidosulphonyl)phenyl]-1-ethyl-3-propyl-1,6-dihydro-7H-pyrazolo(4,3-d)pyrimidin-7-one, 5-[2-ethoxy-5-(4-pyridylamidosulphonyl)phenyl]-1-methyl-3-isobutyl-1,6-dihydro-7H-pyrazolo(4,3-d)pyrimidin-7-one, 5-[2-ethoxy-5-(3-pyridylamidosulphonyl)phenyl]-1-methyl-3-propyl-1,6-dihydro-7H-pyrazolo(4,3-d)pyrimidin-7-one, 5-[2-propyloxy-5-(3-pyridylamidosulphonyl)phenyl]-1-methyl-3-propyl-1,6-dihydro-7H-pyrazolo(4,3-d)pyrimidin-7-one, 5-[2-ethoxy-5-(3-pyridylamidosulphonyl)phenyl]-1-ethyl-3-propyl-1,6-dihydro-7H-pyrazolo(4,3-d)pyrimidin-7-one, 5-[2-ethoxy-5-(3-pyridylamidosulphonyl)phenyl]-1-methyl-3-isobutyl-1,6-dihydro-7H-pyrazolo(4,3-d)pyrimidin-7-one, 5-[2-propyloxy-5-(4-pyridylmethylamidosulphonyl)phenyl]-1-methyl-3-propyl-1,6-dihydro-7H-pyrazolo(4,3-d)pyrimidin-7-one, 5-[2-ethoxy-5-(4-pyridylmethylamidosulphonyl)phenyl]-1-methyl-3-isobutyl-1,6-dihydro-7H-pyrazolo(4,3-d)pyrimidin-7-one, 5-[2-ethoxy-5-(3-pyridylmethylamidosulphonyl)phenyl]-1-methyl-3-propyl-1,6-dihydro-7H-pyrazolo(4,3-d)pyrimidin-7-one, 5-[2-ethoxy-5-(3-pyridylmethylamidosulphonyl)phenyl]-1-methyl-3-isobutyl-1,6-dihydro-7H-pyrazolo(4,3-d)pyrimidin-7-one, 5-[2-propyloxy-5-(3-pyridylmethylamidosulphonyl)phenyl]-1-methyl-3-propyl-1,6-dihydro-7H-pyrazolo(4,3-d)pyrimidin-7-one, 5-[2-ethoxy-5-(2-pyridylmethylamidosulphonyl)phenyl]-1-methyl-3-isobutyl-1,6-dihydro-7H-pyrazolo(4,3-d)pyrimidin-7-one, 5-[2-propyloxy-5-(2-pyridylmethylamidosulphonyl)phenyl]-1-methyl-3-propyl-1,6-dihydro-7H-pyrazolo(4,3-d)pyrimidin-7-one, 5-[2-propyloxy-5-(1-methyl-3-pyrrolidinylamidosulphonyl)phenyl]-1-methyl-3-propyl-1,6-dihydro-7H-pyrazolo(4,3-d)pyrimidin-7-one, 5-[2-ethoxy-5-(1-methyl-3-pyrrolidinylamidosulphonyl)phenyl]-1-methyl-3-isobutyl-1,6-dihydro-7H-pyrazolo(4,3-d)pyrimidin-7-one, 5-[2-propyloxy-5-(1-methyl-2-pyrrolidinylmethylamidosulphonyl)phenyl]-1-methyl-3-propyl-1,6-dihydro-7H-pyrazolo(4,3-d)pyrimidin-7-one, 5-[2-ethoxy-5-(1-methyl-2-pyrrolidinylmethylamidosulphonyl)phenyl]-1-methyl-3-isobutyl-1,6-dihydro-7H-pyrazolo(4,3-d)pyrimidin-7-one, 5-[2-propyloxy-5-(1-methyl-3-pyrrolidinylmethylamidosulphonyl)phenyl]-1-methyl-3-propyl-1,6-dihydro-7H-pyrazolo(4,3-d)pyrimidin-7-one, 5-[2-ethoxy-5-(1-methyl-3-pyrrolidinylmethylamidosulphonyl)phenyl]-1-methyl-3-isobutyl-1,6-dihydro-7H-pyrazolo(4,3-d)pyrimidin-7-one, 5-[2-propyloxy-5-(1-ethyl-3-pyrrolidinylmethylamidosulphonyl)phenyl]-1-methyl-3-propyl-1,6-dihydro-7H-pyrazolo(4,3-d)pyrimidin-7-one, 5-[2-ethoxy-5-(1-ethyl-3-pyrrolidinylmethylamidosulphonyl)phenyl]-1-methyl-3-isobutyl-1,6-dihydro-7H-pyrazolo(4,3-d)pyrimidin-7-one, 5-[2-propyloxy-5-(1-methyl-2-pyrrolidinylethylamidosulphonyl)phenyl]-1-methyl-3-propyl-1,6-dihydro-7H-pyrazolo(4,3-d)pyrimidin-7-one, 5-[2-ethoxy-5-(1-methyl-2-pyrrolidinylethylamidosulphonyl)phenyl]-1-methyl-3-isobutyl-1,6-dihydro-7H-pyrazolo(4,3-d)pyrimidin-7-one, or a pharmaceutically acceptable salt, solvate, or hydrate thereof.

3. The method of claim 2, wherein the PDE5 inhibitor is at least one of 5-[2-ethoxy-5-(4-methylpiperazinylsulphonyl)phenyl]-1-methyl-3-n-propyl-1,6-dihydro-7H-pyrazolo[4,3-d]pyrimidin-7-one (sildenafil) or 5-[2-propyloxy-5-(1-methyl-2-pyrrolidinylethylamidosulphonyl)phenyl]-1-methyl-3-propyl-1,6-dihydro-7H-pyrazolo(4,3-d)pyrimidin-7-one (udenafil) or a pharmaceutically acceptable salt, solvate, or hydrate thereof.

* * * * *